United States Patent [19]
Farng et al.

[11] Patent Number: 5,171,465
[45] Date of Patent: Dec. 15, 1992

[54] PHENYLENEDIAMINE-DERIVED PHOSPHONATES AS MULTIFUNCTIONAL ADDITIVES FOR LUBRICANTS

[75] Inventors: Liehpao O. Farng, Lawrenceville; Andrew G. Horodysky, Cherry Hill, both of N.J.

[73] Assignee: Mobil Oil Corporation, Fairfax, Va.

[21] Appl. No.: 841,284

[22] Filed: Feb. 28, 1992

Related U.S. Application Data

[63] Continuation of Ser. No. 521,612, May 10, 1990, abandoned.

[51] Int. Cl.$^5$ ............................................. C10M 137/02
[52] U.S. Cl. .................................. 252/49.9; 252/400.2
[58] Field of Search ........................................ 252/49.9

[56] References Cited

U.S. PATENT DOCUMENTS

| | | | |
|---|---|---|---|
| 3,549,728 | 12/1970 | Balde et al. | 252/49.9 |
| 4,016,092 | 4/1977 | Andress | 252/49.9 |
| 4,331,546 | 5/1982 | Frangatos | 252/49.9 |
| 4,563,299 | 1/1986 | Frangatos | 252/49.9 |
| 4,615,826 | 10/1986 | Erdman | 252/32.5 |
| 4,806,130 | 2/1989 | Chibnik | 44/63 |

*Primary Examiner*—Jacqueline Howard
*Attorney, Agent, or Firm*—Alexander J. McKillop; Charles J. Speciale; Jessica M. Sinnott

[57] ABSTRACT

A lubricant contains an antioxidant and antiwear amount of a Mannich base reaction product of a phenylenediamine, such as N,N'-dihydrocarbyl substituted phenylenediamine, an aldehyde or ketone and a dialkyl-substituted phosphonate such as dimethyl hydrogen phosphonate or bis(2-ethylhexyl) hydrogen phosphonate.

11 Claims, No Drawings

PHENYLENEDIAMINE-DERIVED PHOSPHONATES AS MULTIFUNCTIONAL ADDITIVES FOR LUBRICANTS

This is a continuation of copending application Ser. No. 07/521,612, filed on May 10, 1990, now abandoned.

FIELD OF THE INVENTION

The invention relates to lubricants. Specifically, the invention relates to reaction products of arylamines, carbonyl compounds and di-hydrocarbyl-substituted phosphonate compounds as multifunctional antioxidant and antiwear additives for blending with lubricants. The invention also relates to lubricant compositions containing the reaction products and methods of making the same.

BACKGROUND OF THE INVENTION

Under normal operating and storage conditions, lubricants are subject to high temperatures and oxygen which leads to oxidation and decomposition of the lubricant. Oxidation of a lubricant can lead to the build-up of oil-soluble acids, lacquers and sludge which cause serious damage to engines and other lubricated systems. Typically, antioxidant additives are blended with lubricants in order to improve the stability of the lubricant and thereby enhance the ability of the oil to resist oxidation.

Additionally, mechanical systems under heavy loads will deteriorate due to the frictional forces created by relatively moving and bearing metal surfaces. Often, lubricants for such operations cannot prevent wear of the metal and as a result the performance of the system is adversely affected. Often, antiwear additives are blended with lubricants in order to prevent wear and increase the operating life of the systems.

The reaction products of preformed Mannich bases and dithiophosphoric acids having at least one reactive hydrogen have been described as antioxidants and antiwear additives in lubricants, fuels and plastics in U.S. Pat. No. 4,806,130.

SUMMARY OF THE INVENTION

It has now been found that the Mannich base reaction products of arylamines, carbonyl compounds and dihydrocarbyl-substituted phosphonate compounds are effective multifunctional antioxidant and antiwear additives in lubricants. It is also believed that the multifunctional additives of the present invention are effective antioxidants and antiwear additives and may also provide friction reducing, detergent, antifatigue and/or anticorrosion properties.

The arylamines of the present invention are ortho-, meta- or para-phenylenediamines, N-hydrocarbyl-substituted-phenylenediamines and N,N'-dihydrocarbyl-substituted-phenylenediamines having the following structural formula:

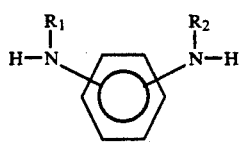

where $R_1$ and $R_2$ are the same or different, hydrogen atom or aliphatic or aromatic hydrocarbyl containing 1 to 60 carbon atoms or at least one heteroatom such as oxygen, sulfur or nitrogen bonded to hydrocarbyl containing 2 to 60 carbon atoms. Also contemplated are the N,N, N'-trihydrocarbyl-substituted phenylenediamines in which there is only one free hydrogen atom bonded to either nitrogen atom of the phenylenediamine and the hydrocarbyl substituents are of the kind indicated above. At least one free hydrogen atom bonded to the nitrogen atom is necessary in order for the aryl amine to react with the carbonyl compound. It is further contemplated that the arylamine can also contain alkyl, aryl or aralkyl groups bonded directly to the large nucleus of the amine. Representative phenylenediamines are toluene-2,4-diamine phenylenediamine, toluene-2,6-diamine phenylenediamine, 2,3,5,6-tetra-methyl-p-phenylenediamine, N,N'dimethyl-p-phenylenediamine, N,N'-diethyl-p-phenylenediamine, N,N'-di-sec-butyl-p-phenylenediamine, N,N'-bis(1-methyl-heptyl)-p-phenylenediamine, N,N'di-sec-butyl-N,N'dimethyl-p-phenylenediamine, N-phenyl-p-phenylenediamine, N,N'-diphenyl-p-phenylenediamine, N,N'-di-2-naphthyl-p-phenylenediamine, N-isopropyl-N'-phenyl-p-phenylenediamine, N-(1,3-dimethyl-butyl)-N'-phenyl-p-phenylenediamine, N-cyclohexyl-N'-phenyl-p-phenylenediamine. A preferred phenylenediamine is N,N'-bis(1,4-dimethylpentyl)-p-phenylenediamine which is commercially available from Uniroyal Chemical Company under the trade name NAUGALUBE 443.

The carbonyl compounds of the present invention are aldehydes or ketones having the structural formula:

where $R_3$ and $R_4$ are the same, or different, hydrogen atom or aliphatic or aromatic hydrocarbyl containing 1 to 60 carbon atoms or at least one heteroatom such as oxygen, sulfur or nitrogen bonded to hydrocarbyl containing from 2 to 60 carbon atoms. Representative examples of carbonyl compounds are formaldehyde, acetaldehyde, propanaldehyde, paraformaldehyde, benzaldehyde, butyraldehyde, salicylaldehyde, hexaldehyde, heptaldehyde, acetone, diethyl ketone and methyl ethyl ketone. The preferred carbonyl compound is formaldehyde.

The dihydrocarbyl-substituted phosphonate compounds have the structural formula

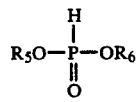

where $R_5$ and $R_6$ are the same or different, aliphatic or aromatic hydrocarbyl containing 1 to 60 carbon atoms or at least one heteroatom such as oxygen, sulfur, nitrogen or boron bonded to hydrocarbyl containing 2 to 60 carbon atoms. The phosphonates contemplated also have a reactive hydrogen. The preferred phosphonates are dibutyl hydrogen phosphonate, dimethyl hydrogen phosphonate and bis(2-ethylhexyl) hydrogen phosphonate which is commercially available form Albright and Wilson, Inc. The phosphonates of the present invention are made by known methods, typically, from $PCl_3$ and hydroxy compounds such as alcohols, phenols or naphthols.

The reactants combine in a condensation reaction to form a Mannich base. Water is formed during the condensation reaction: one mole of water is released for each mole of Mannich base condensation product formed so that the evolution of water can be utilized to monitor the course of the reaction. The reaction can be carried-out in any manner known in the art. However, in the preferred method, the Mannich base is formed by contacting the amine and the carbonyl compound in a mixture and the temperature is elevated to a point which is sufficient to effect the reaction. Typically, the reaction will proceed at ambient pressure and at temperatures ranging from about 50° C. to 400° C. The preferred temperature ranges from about 65° C. to 175° C. the reaction time can range from 0.25 to 48 hours, the preferred reaction time being 10 hours. Thereafter, the phosphonate is added along with a diluent or solvent such as methanol. The temperature of the mixture can be maintained in a range of 50° C. to 400° C., preferably from 70° C. to 150° C. The components can be reacted in proportions expressed in a molar ratio of arylamine to carbonyl compound to phosphonate of 0.5:1.0:0.5 to 1:4:4, preferably of 0.7:2:0.7 to 1:3:3. The reactants are contacted for such time and at such temperature that water of reaction ceases to be produced. Typically, the temperature can be raised incrementally to increase the rate of reaction and maintained for such time that the reaction is substantially complete which is indicated by the lack of formation of water.

Since the reactant molecules permit the reaction to take place at several sites, a number of different product structures may be obtained. Typically the product contains an alkylphosphonate in which there is a phosphorus-carbon linkage. The carbon of the phosphorus-carbon linkage is bonded to the arylamine by condensation occurring directly on the nitrogen or carbon of the arylamine. Although the exact structure of the products is not known, it is believed that in general, the structure of the products may be represented by the formula:

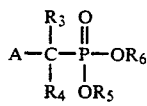

in which $R_3$, $R_4$, $R_5$ and $R_6$ are as described above and A is the arylamine which has been described above.

Specific types of structures which may be produced include:

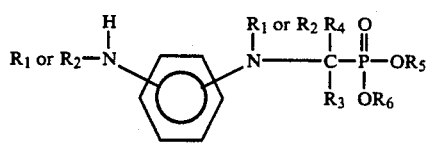

Other structures may be formed by condensation occurring directly on the nucleus of the diamine as in:

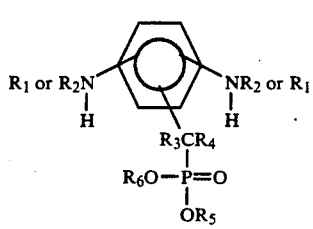

The reaction products are blended with lubricants in a concentration of about 0.01% to 10%, preferably, from 0.05% to 5% by weight of the total composition.

An important feature of the invention is the ability of the additive to improve the oxidation resistance of the lubricant. Arylamines are known antioxidant additives for lubricant, polymer and rubber applications. Similarly, phosphonate derivatives are known multifunctional antioxidant, antiwear, load carrying and metal stabilizing additives for lubricant applications. Thus, it is believed that the effectiveness of the reaction products of the present invention is due to the activity of the amine group and the phosphonate group which is enhanced by the alkyl linkage derived from the carbonyl compound and which facilitates synergistic antioxidant activity between the amine and the phosphonate. It is also believed that the reaction products have improved load carrying capabilities and metal deactivating properties which are contributed by the phosphonate group.

The contemplated lubricants are liquid oils in the form of either a mineral oil or synthetic oil or mixtures thereof. Also contemplated are greases in which any of the foregoing oils are employed as a base. Still further materials which it is believed would benefit from the rection products of the present invention are fuels and plastic materials.

In general, the mineral oils, both paraffinic and naphthenic and mixtures thereof can be employed as a lubricating oil or as the grease vehicle. The lubricating oils can be of any suitable lubrication viscosity range, for example, from about 45 SSU at 100° F. to about 6000 SSU at 100° F., and preferably from about 50 to 250 SSU at 210° F. Viscosity indexes from about 70 to 95 being preferred. The average molecular weights of these oils can range from about 250 to about 800.

Where the lubricant is employed as a grease, the lubricant is generally used in an amount sufficient to balance the total grease composition, after accounting for the desired quantity of the thickening agent, and other additive components included in the grease formulation. A wide variety of materials can be employed as thickening or gelling agents. These can include any of the conventional metal salts or soaps, such as calcium, or lithium stearates or hydroxystearates, which are dispersed in the lubricating vehicle in grease-forming quantities in an amount sufficient to impart to the resulting grease composition the desired consistency. Other thickening agents that can be employed in the grease formulation comprise the non-soap thickeners, such as surface-modified clays and silicas, aryl ureas, calcium complexes and similar materials. In general, grease thickeners can be employed which do not melt or dissolve when used at the required temperature within a particular environment; however, in all other respects, any material which is normally employed for thickening or gelling hydrocarbon fluids for forming greases can be used in the present invention.

Where synthetic oils, or synthetic oils employed as the vehicle for the grease are desired in preference to mineral oils, or in mixtures of mineral and synthetic oils, various synthetic oils may be used. Typical synthetic oils include polyisobutylenes, polybutenes, hydrogenated polydecenes, polypropylene glycol, polyethylene glycol, trimethylol propane esters, neopentyl and pentaerythritol esters, di(2-ethylhexyl) sebacate, di(2-ethylhexyl) adipate, dibutyl phthalate, fluorocarbons, silicate esters silanes, esters of phosphorus-containing acids, liquid ureas, ferrocene derivatives, hydrogenated synthetic oils, chain-type polyphenyls, siloxanes and silicones (polysiloxanes) and alkyl-substituted diphenyl ethers typified by a butyl-substituted bis(p-phenoxy phenyl) ether and phenoxy phenylethers.

The lubricating oils and greases contemplated for blending with the reaction product can also contain other additive materials such as corrosion inhibitors, detergents, extreme pressure agents, viscosity index improvers, friction reducers, antiwear agents and the like.

When the additives are utilized in fuels, the fuels contemplated are liquid hydrocarbon and liquid oxygenated fuels such as alcohols and ethers. The additives can be blended in a concentration from about 0.01% to about 10 wt. % based on the total weight of the fuel composition. Preferably, the concentration is from 0.1 to about 5 wt. %.

EXAMPLE 1

Approximately 153 g (0.5 mole) N,N'-bis(1,4-dimethylpentyl) para-phenylenediamine (commercially available from Uniroyal Chemical Company under trade name NAUGALUBE 443) and 85 g (1.05 mole) aqueous formaldehyde (37 wt. % solution) were mixed in a reactor equipped with heater, agitator, thermometer, and Dean Stark tube with condenser. The reactants were heated at 70° C. for one hour. Thereafter, 110 g (1.0 mole) dimethyl hydrogen phosphonate (dimethyl phosphite) and 100 ml of methanol were added, and this mixture was heated at 70°-75° C. for two hours, at 110°-110° C. for eight hours during which methanol and water were collected in the Dean Stark condenser. Finally, the solution was filtered through diatomaceous earth to produce a dark fluid (275.6 g) as desired product.

EXAMPLE 2

Approximately 30.6 g (0.1 mole) N,N'-bis(1,4-dimethylpentyl) para-phenylenediamine (NAUGALUBE 443) and 16.5 g (0.23 mole) aqueous formaldehyde (37 wt. % solution) were charged in a four-neck flask, and the reactants were stirred at 70° C. for an hour. Then 61.2 g (0.2 mole) Bis(2-ethylhexyl) phosphite (commercial chemical from Albright and Wilson Inc.) and 100 ml of methanol were added, and the mixture was refluxed at boiling methanol over a course of two hours. Thereafter, the reaction temperature was gradually increased from 75° C. to 100° C., while removing volatiles through a condenser. One additional hour of heating at 150° C. produced no more water of reaction. The final liquid was filtered through diatomaceous earth to isolate 77.6 g of the desired product.

EVALUATION OF THE PRODUCT

The reaction product was blended in a concentration of 1 wt. % in a mineral oil and evaluated for antioxidant performance in the B-10 Catalytic Oxidation Test at 325° F. for 40 hours (Table 1) and in the B-10 Catalytic Oxidation Test at 325° F. for 72 hours (Table 2). A comparison of the oxidation-inhibiting characteristics of the products of the present invention with other traditional antioxidants in the same mineral oil was also included in Tables 1 and 2.

The product of Example 1 was blended into a mineral oil sample and evaluated for oxidative stability in the B-10 Catalytic Oxidation Test. In the Catalytic Oxidation Test, the tests were run at 325° F. for 40 hours (Table I) and at 325° F. for 72 hours (Table II). The test procedure consisted of subjecting a volume of the test lubricant to a stream of air which was bubble through the test composition at a rate of about 5 liters per hour for the specified number of hours and at the specified temperature. Present in the test composition were metals frequently found in engines, namely:
1) 15.5 square inches of a sand-blasted iron wire;
2) 0.78 square inches of a polished copper wire;
3) 0.87 square inches of a polished aluminum wire; and
4) 0.107 square inches of a polished lead surface.

The results of the test were presented in terms of change in kinematic viscosity (KV), change in neutralization number (TAN) and lead loss. Essentially, the small change in KV meant that the lubricant maintained its internal resistance to flow under high temperatures, the small change in TAN indicated that the oil maintained its acidity level under oxidizing conditions and the small change in lead loss indicated that the lubricant was not corrosive to lead under corrosive conditions, such as high temperatures and oxidizing conditions.

The products of Examples 1 and 2 were also tested for their ability to resist corrosion of copper in the Copper Strip Corrosivity Test. The test consisted of immersing a polished copper strip in a given quantity of a sample of the test composition. The sample was heated to 250° F. At the end of 3 hours the copper strip was removed, washed and compared with the ASTM Copper Strip Corrosion Standards. The Corrosion Standards consisted of color reproductions of typical test strips representing increasing degrees of tarnish and corrosion which were noted in accordance with four specific classifications which ranged from 1, the highest score representing slight tarnish, to 4, the lowest score representing actual corrosion. The corrosivity ratings attained by the test compositions were reported in Table 3. The test sample containing the product of Example 1 achieved a 1A rating and the test sample containing the product of Example 2 achieved a 2A rating. These ratings indicated that the products of the examples were superlative in resisting corrosion of copper.

The ability of the oil containing the additives of the present invention to prevent the wearing down of metal parts under severe operating conditions was tested in the Shell 4-Ball Wear Test. The results of the test were presented in Table 4. Following the standard ASTM testing procedure, the test was conducted in a device comprising four steel balls, three of which were in contact with each other in one plane in a fixed triangular position in a reservoir containing the test sample. The fourth ball was above and in contact with the other three. The fourth ball was rotated at 2000 rpm while under an applied load of 60 kg, it was pressed against the other three balls, the pressure was applied by weight and lever arms. The tests were conducted at 200° F. for 30 minutes. The diameter of the scar on the other three lower balls was measured with a low power microscope and the average diameter measured in two directions on each of the three lower balls was taken as a measure of the antiwear characteristics of the test composition. Table 4 shows the marked decrease in wear scar diameter obtained with respect to the test composition containing the product of Example 2.

TABLE 1

| | Catalytic Oxidation Test 40 Hours at 325° F. | | | | |
|---|---|---|---|---|---|
| Item | Additive Conc. (wt %) | Change In Acid Number ΔTAN | Percent Change In Viscosity % ΔKV | Lead Loss | Sludge |
| Base Oil (200 second, solvent refined, paraffinic neutral, mineral oil) | — | 4.78 | 57.9 | 2.9 | Heavy |
| Example 1 | 1.0 | 0.25 | 1.6 | 0.0 | Light |
| Commercial Arylamine Antioxidant (Irganox L-57) (Ciba-Geigy) | 1.0 | 1.26 | 11.2 | 0.0 | Trace |
| Commercial Phenolic Antioxidant (Irganox L-130) (Ciba-Geigy) | 1.0 | 5.31 | 45.1 | 0.0 | Heavy |
| Commercial 4,4'-Methylene bis (2,6-di-t-butyl) phenol | 1.0 | 6.24 | 62.4 | 0.0 | Heavy |

TABLE 2

| | Catalytic Oxidation Test 72 Hours at 325° F. | | | |
|---|---|---|---|---|
| Item | Additive Conc. (wt %) | Change In Acid Number ΔTAN | Percent Change In Viscosity % ΔKV | Lead Loss |
| Base Oil (200 second, solvent refined, paraffinic neutral, mineral oil) | — | 8.53 | 99.4 | 5.2 |
| Example 1 | 1.0 | 1.45 | 10.8 | 0.0 |
| Commercial Phenolic Antioxidant (Irganox L-130) | 1.0 | 6.48 | 58.1 | 0.0 |
| Commercial 4,4'-Methylene bis (2,6-di-t-butyl) phenol | 1.0 | 7.13 | 101.3 | 0.0 |
| Commercial Arylamine Antioxidant (Irganox L-57) | 1.0 | 6.14 | 79.1 | 0.0 |

TABLE 3

| | (D130-6) Copper Strip Corrosivity Test (250° F.) | |
|---|---|---|
| Item | Additive conc. (wt %) | Corrosivity Rating |
| Base Oil (200 second, solvent refined, paraffinic neutral, mineral oil) | — | 1A/1B |
| Example 1 | 1.0 | 1A |
| Example 2 | 1.0 | 2A |

TABLE 4

| | Four-Ball Wear Test (60 kg, 2000 rpm, 30 min., 200° F.) |
|---|---|
| Item | Wear Scar Diameter (mm) |
| Base Oil (80% solvent refined paraffinic bright oil, 20% solvent refined paraffinic neutral oil) | 3.98 |
| 1% Example 2 | 0.55 |

What is claimed is:

1. A lubricant composition comprising a major amount of an oil of lubricating viscosity or grease prepared therefrom and an amount sufficient to impart multifunctional antiwear properties to the oil of a reaction product for blending with the oil, comprising the reaction product of a phenylenediamine which is N,N'-di-sec-butyl-p-phenylenediamine N,N'-bis(1,4-dimethylpentyl)-p-phenylenediamine, a carbonyl compound and a dihydrocarbyl-substituted phosphonate compound.

2. The composition of claim 1 in which the carbonyl compound has the following structural formula:

$$R_3R_4C=O$$

where $R_3$ and $R_4$ are the same or different, hydrogen atom, or hydrocarbyl containing 1 to 60 carbon atoms.

3. The composition of claim 1 in which the carbony compound is formaldehyde, acetaldehyde, propionaldehyde, paraformaldehyde, benzaldehyde, butyraldehyde, salicylaldehyde, hexaldehyde, heptaldehyde, acetone, diethyl ketone or methyl ethyl ketone.

4. The composition of claim 1 in which the dihydrocarbyl-substituted phosphonate compound has the following structural formula:

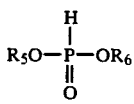

where $R_5$ and $R_6$ are the same or different hydrocarbyl group containing 1 to 60 carbon atoms.

5. The composition of claim 4 in which the phosphonate compound is dibutyl hydrogen phosphonate, dimethyl hydrogen-phosphonate or bis(2-ethylhexyl) hydrogen-phosphonate.

6. A lubricant composition comprising a major amount of an oil of lubricating viscosity or grease prepared therefrom and an amount sufficient to impart multifunctional antiwear properties to the oil of a reaction product of a phenylenediamine having the structural formula

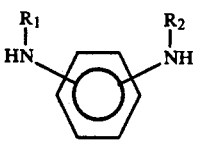

where $R_1$ and $R_2$ are alkyl groups containing 7 to 60 carbon atoms, a carbonyl compound and a dihydrocarbyl-substituted phosphonate.

7. The composition of claim 6 in which $R_1$ and $R_2$ are each 1,4-dimethylpentyl.

8. The composition of claim 6 in which the carbonyl compound has the following structural formula:

$$R_3R_4C=O$$

where $R_3$ and $R_4$ are the same or different, hydrogen atom, or hydrocarbyl containing 1 to 60 carbon atoms.

9. The composition of claim 6 in which the carbon 1 compound is formaldehyde, acetaldehyde, propionaldehyde, paraformaldehyde, benzaldehyde, butyraldehyde, salicylaldehyde, hexaldehyde, heptaldehyde, acetone, diethyl ketone or methyl ethyl ketone.

10. The composition of claim 6 in which the dihydrocarbyl-substituted phosphonate compound has the following structural formula:

$$R_5O-\underset{\underset{O}{\overset{\|}{P}}}{\overset{H}{|}}-OR_6$$

where $R_5$ and $R_6$ are the same or different hydrocarbyl group containing 1 to 60 carbon atoms.

11. The composition of claim 10 in which the phosphonate compound is dibutyl hydrogen phosphonate, dimethyl hydrogen-phosphonate or bis(2-ethylhexyl) hydrogen-phosphonate.

* * * * *